United States Patent [19]
Geddes et al.

[11] Patent Number: 4,979,948
[45] Date of Patent: Dec. 25, 1990

[54] METHOD AND APPARATUS FOR THERMALLY DESTROYING A LAYER OF AN ORGAN

[75] Inventors: Leslie A. Geddes, West Lafayette; Marvin H. Hinds, Marion; Joe D. Bourland; William D. Voorhees, both of West Lafayette, all of Ind.

[73] Assignees: Purdue Research Foundation, West Lafayette; Med Institute, Inc., West Lafayette, both of Ind.

[21] Appl. No.: 337,356

[22] Filed: Apr. 13, 1989

[51] Int. Cl.⁵ ..................... A61B 17/39; A61N 5/00
[52] U.S. Cl. ..................... 606/33; 128/401; 128/786; 128/804
[58] Field of Search ............. 128/303.17, 303.13, 128/784, 785, 786, 804, 401; 606/33, 49

[56] References Cited

U.S. PATENT DOCUMENTS

| | | | |
|---|---|---|---|
| 4,643,186 | 2/1987 | Rosen et al. | 128/303.1 |
| 4,662,383 | 5/1987 | Sogawa et al. | 128/401 X |
| 4,676,258 | 6/1987 | Inokuchi et al. | 128/804 |
| 4,681,117 | 7/1987 | Brodman et al. | 128/642 |
| 4,709,698 | 12/1987 | Johnston et al. | 128/303.12 |

FOREIGN PATENT DOCUMENTS

| | | | |
|---|---|---|---|
| 0251745 | 1/1988 | European Pat. Off. | 128/804 |
| 3516830 | 11/1986 | Fed. Rep. of Germany | 128/786 |
| 1093347 | 5/1984 | U.S.S.R. | 128/784 |

OTHER PUBLICATIONS

Becker et al., "Long-Term Occlusion of the Porcine Cystic Duct by Means of Endoluminal Radio-Frequency Electrocoagulation," *Radiology*, vol. 167, No. 1, Apr. 1988, pp. 63–68.

Becker et al., "Can the Newer Interventional Procedures Replace Cholecystectomy for Cholecystolithiasis?," *Radiology*, vol. 167, No. 1, Apr. 1988, pp. 275–279.

Primary Examiner—Lee S. Cohen
Attorney, Agent, or Firm—Richard J. Godlewski

[57] ABSTRACT

Method and apparatus are disclosed for thermally destroying a layer of an organ such as the mucosal layer of the gallbladder. The apparatus includes a catheter having an elongated member having a plurality of lumens therein. At the distal end of the elongated member is an electrode for emitting radiofrequency current to the mucosal layer. Also at the distal end is a capacitive balloon electrode surrounding the current-emitting electrode for containing an electrolyte solution and for distributing the radiofrequency current to the mucosal layer. The balloon electrode is expanded with the electrolyte solution to conform and make contact with the mucosal layer. The electrolyte solution has a resistivity significantly less than the resistivity of the gallbladder wall, as well as the gallbladder bile, to cause a concentrated power deposition in the mucosal layer. The distal end of the catheter is endoscopically inserted into the body of the gallbladder by a retrograde route through the duodenum, common bile duct and cystic duct. While the balloon electrode is being expanded, the bile present in the gallbladder is drained through one of the lumens in the elongated member. The apparatus also includes a radiofrequency generator for supplying radiofrequency current to the current-emitting electrode. The current-emitting electrode is energized for a period of time to cause the mucosal layer to be heated for a predetermined period of time to thermally coagulate the mucosal layer of the gallbladder and cystic duct. A dispersive electrode is positioned on the skin of the patient's body to facilitate a complete circuit back to the generator without causing trauma to the patient.

22 Claims, 2 Drawing Sheets

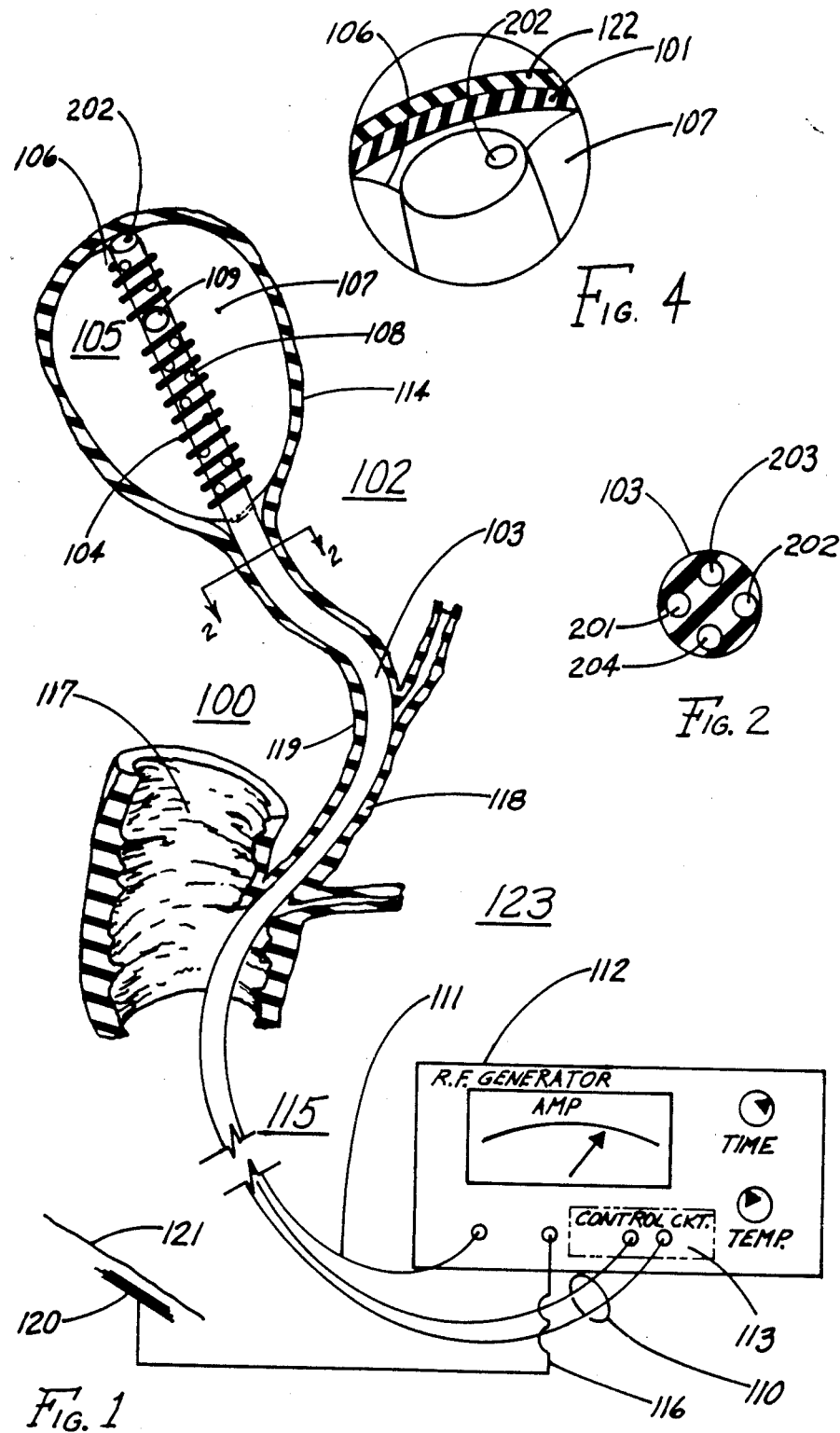

METHOD AND APPARATUS FOR THERMALLY DESTROYING A LAYER OF AN ORGAN

TECHNICAL FIELD

This invention relates to catheters and, in particular, method and apparatus including a catheter for heating the layer of an organ.

BACKGROUND OF THE INVENTION

Gallstones are a common problem in the United States and the most frequent cause of gallbladder inflammation. About 500,000 cholecystectomies are performed each year with an overall medical cost nearing approximately two billion dollars. Patients of all ages with cholecystitis have a mortality rate of 1.3% to 5%. For those over 65 years of age, the rate increases to 10%. When empyema of the gallbladder is present, the mortality rate is close to 29%. As the population ages, there will be more and more poor-risk patients with troublesome gallstones.

Removal of only gallstones, without a cholecystectomy, offers promise of reducing risk, but only solves the problem temporarily. Nearly 50% of the patients having a surgical cholecystostomy with the gallbladder left intact will have a recurrence of gallstones within three years or less, and 80% will develop stones within 15 years. As yet, there are no long-term follow-up studies for nonsurgical removal of gallstones by extracorporeal shockwave lithotripsy or by methyl-tertiary-butyl ether treatment. However, one study evaluating the recurrence of gallstones following another nonsurgical method of removal, bile-acid treatment, found the recurrence rate to be 24% at one year, rising to 58% at two years, 63% at three years, and 100% at five years. Other bile-acid treatment studies have indicated somewhat lower rates of recurrence, but 50% eventual recurrence seems to be generally accepted. Therefore, the need for preventing the recurrence of gallstones is significant. This is further heightened by eliminating the problem with a nonsurgical solution that will reduce the costs and the mortality rate associated with surgical methods.

SUMMARY OF THE INVENTION

The foregoing problems are solved and a technical advance is achieved by a method and apparatus for thermally destroying the layer of an organ such as by thermally coagulating the mucosal layer of the gallbladder to reduce, if not eliminate, the recurrence of gallstones. Illustratively, the apparatus includes a catheter comprising an elongated member having a current-emitting electrode positioned about the distal end thereof for emitting radiofrequency current. The catheter also includes a capacitive balloon electrode that is positioned about the distal end of the elongated member and surrounds the current-emitting electrode for performing a number of advantageous functions. First, the balloon electrode distributes the radiofrequency current from the current-emitting electrode to the layer. This facilitates a more uniform distribution of the emitted current to the mucosal layer. Next, the balloon electrode is expanded with an electrolyte solution for making contact with the mucosal layer and for containing the electrolyte solution. The electrolyte solution has a resistivity less than the resistivity of the mucosal layer for selectively heating the mucosal layer.

The change in resistivity from a lesser to a higher level at the interface of the electrolyte solution and the mucosal layer causes a concentrated deposition of power within the mucosal layer of the gallbladder. The degree of resistivity change at the interface controls the concentration of power deposited in the mucosal layer and consequently the selective heating of the mucosal layer. The greater is the resistivity change; the greater is the concentration of power in the mucosal layer. Furthermore, a power deposition peak occurs at the interface of the electrolyte solution and the mucosal layer.

The capacitive balloon electrode is also expanded for conforming the shape of the gallbladder and the balloon electrode together. This brings the capacitive balloon electrode in physical and electrical contact with the mucosal layer for distributing the radiofrequency current to the mucosal layer in a more uniform manner. The balloon electrode also contains the electrolyte solution and brings the solution within close proximity of the mucosal layer. As a result, electrolyte solutions that have resistivity levels much lower than that of the mucosal layer, as well as the gallbladder bile, may be used to expand the balloon electrode. This containing feature is particularly advantageous since some of the lower resistivity level solutions are caustic to the surrounding tissue. These lower resistivity level solutions can also be made radio-opaque, thereby allowing fluoroscopic visualization of the balloon electrode in the gallbladder prior to applying the radiofrequency current. A filling lumen extending longitudinally through the elongated member and a plurality of sideports about the distal end thereof are utilized to fill and expand the balloon electrode with the electrolyte solution.

A second lumen is also provided in the elongated member for draining the bile from the gallbladder as the balloon electrode expands. Draining the bile from the gallbladder permits the lower resistivity level electrolyte solution to be positioned in close proximity to the mucosal layer.

The wall of the balloon electrode comprises a relatively thin flexible material such as latex which has a relatively large predetermined capacitance. Consequently, the impedance of the capacitive balloon electrode to the radiofrequency current is relatively low. The radiofrequency current is thus negligibly impeded by the capacitive balloon electrode.

The catheter also includes a sensor positioned about the distal end of the member for sensing a temperature of an environment about the distal end. Illustratively, this sensor includes a thermistor for sensing the temperature of the current-emitting electrode and the surrounding electrolyte solution which is indicative of the temperature of the mucosal layer. A pair of electrical conductors connected to the thermistor extends through a third lumen in the elongated member to a control circuit. In response to the sensed temperature, the control circuit regulates the amount of radiofrequency current supplied by a generator to the current-emitting electrode.

The radiofrequency current is supplied to the current-emitting electrode via a conductor extending through a fourth lumen in the elongated member to the current-emitting electrode.

The apparatus also includes the radiofrequency current generator and the control circuit that cooperate to supply current to the current-emitting electrode. The electrode is used to heat the mucosal layer of the gallbladder to a predetermined temperature for a predetermined period of time to thermally coagulate the mucosal layer. Consequently, the mucosal layer is thermally destroyed along with the mucosal layer of the cystic duct for advantageously preventing the recurrence of gallstones within the gallbladder. The selective deposition of power in the mucosal layer also prevents thermal destruction of the outside wall of the gallbladder and the surrounding tissue.

To significantly reduce the risks associated with surgery, the method of the invention includes inserting the distal end of the catheter endoscopically into the gallbladder by a retrograde route through the duodenum, common bile duct and cystic duct.

BRIEF DESCRIPTION OF THE DRAWINGS

FIG. 1 depicts apparatus inserted in the body of the gallbladder for thermally destroying the mucosal layer thereof; FIG. 2 depicts a cross-sectional view of the elongated member of the apparatus of FIG. 1;

FIG. 4 depicts an enlarged view of the distal end of the elongated member of the apparatus of FIG. 1.

DETAILED DESCRIPTION

Figure 3:
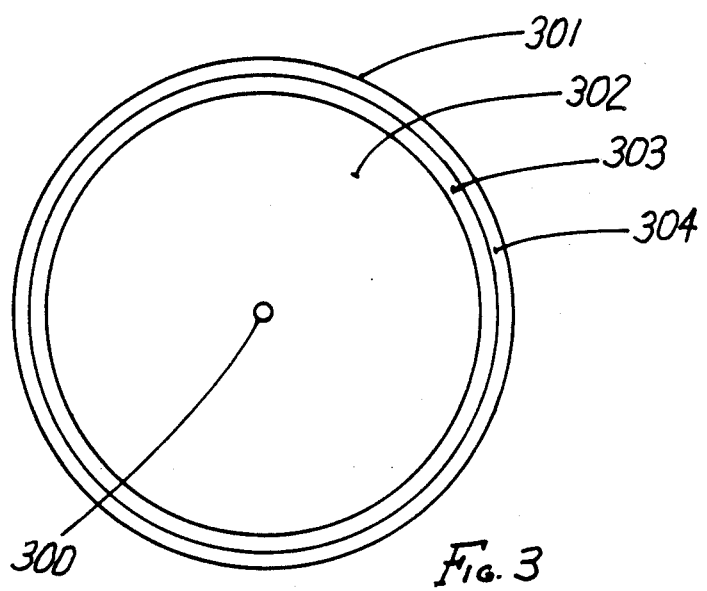
FIGS. 3 and 5 depict a spherical model of a gallbladder and the power deposition at a radial distance from a central electrode placed in the spherical model.

Depicted in FIG. 1 is illustrative apparatus 123 including a catheter 100 having a distal end 105 that is inserted into an organ such as body 114 of gallbladder 102 for thermally coagulating and destroying the inner mucosal layer 101 of the gallbladder. The distal end of the catheter is endoscopically introduced into the body of the gallbladder by a retrograde route through the duodenum 117, common bile duct 118, and cystic duct 119. Catheter 100 includes an elongated member 103 with a current-emitting electrode 104 positioned about the distal end thereof for emitting radiofrequency current to the mucosal layer of the gallbladder. Also positioned about the distal end of the elongated member and surrounding the current-emitting electrode is capacitive balloon electrode 106, which is expandable for making physical and electrical contact with the mucosal layer of the gallbladder.

The balloon electrode is expanded with an electrolyte solution 107 that has a resistivity level less than the resistivity level of the mucosal layer for concentrating the deposition of radiofrequency power in the mucosal layer. The mucosal layer 101 of gallbladder 102 has a relatively high level of electrical resistivity approximating, for example, 500 ohm-cm. The electrical resistivity of the electrolyte solution is at a much lower level and approximates, for example, 10 ohm-cm. The solution resistivity is also selected to be less than the resistivity of the gallbladder bile, which typically approximates 70 ohm-cm. The change in resistivity from 10 ohm-cm to 500 ohm-cm represents a significant gradient in the order of one and a half orders of magnitude. The radiofrequency heating method of this invention exploits this low-to-high level change in electrical resistivity from the electrolyte solution to the mucosal layer at the interface thereof. A large change in resistivity causes a concentrated power deposition in the inner mucosal layer of the gallbladder, because there is greater power dissipation in media of higher electrical resistivity. It is this power deposition as a function of distance from the current-emitting electrode that produces selective heating.

Figure 5:
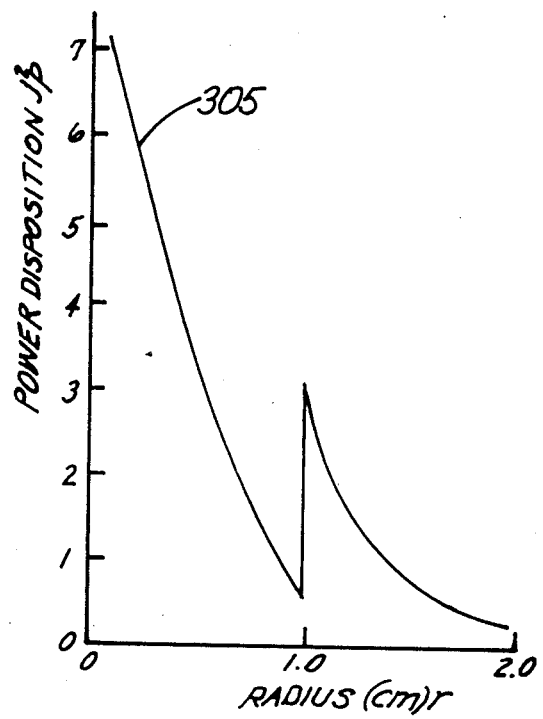

A spherical model of a gallbladder is depicted in FIG. 3 to illustrate the selective heating feature of the invention. A current-emitting point electrode 300 is positioned at the center of a spherical gallbladder 301 of 1.0 cm inner radius filled with bile 302 having a resistivity of 70 ohm-cm. Beyond 1 cm is the inner mucosal layer 303 and outer gallbladder wall 304 of resistivity approximating 500 ohm-cm. Beyond the outer gallbladder wall is the liver (not shown) with approximately the same resistivity. The deposited power density as a function of radial distance from the electrode is illustrated by curve 305. The deposited power density at any point on curve 305 depicted in FIG. 5 is $J^2 p$, where J is the current density (current I divided by area) and p is the electrical resistivity. At any radius r, the current density $J = I/(4\pi r^2)$. Current density J decreases as the inverse square of the distance from the electrode in the center of the sphere. From the central electrode, the radiofrequency current first encounters the low-resistivity bile and then the high-resistivity bladder wall and extrabladder tissues. It is the deposited power that produces heating. At a distance beyond the bile of the gallbladder (r > 1.0 cm), the current density continues to decrease, but the resistivity rises to a high level such as 500 ohm-cm. Consequently, there is a peak in power deposition in the inner mucosal layer 303 of the gallbladder where the resistivity gradient at the interface is the largest changing from 70 ohm-cm to 500 ohm-cm. As a result, there is a concentration of deposited power in and selective heating of the mucosal layer at the bile-gallbladder interface.

Returning the reader's attention to FIG. 1, balloon electrode 106 is expanded with an electrolyte solution 107 having a resistivity lower than that of the gallbladder bile. This further enhances the resistivity gradient at the interface and more selectively concentrates the power deposition and heating in the mucosal layer. By way of example, the electrolyte solution used to expand balloon electrode 107 comprises a solution of 5% saline with potassium iodide added to provide radio-opacity. The addition of 5 grams of potassium iodide to 100 ml of 5% saline reduces the resistivity of the latter by 25%. The resistivity of the resulting mixture is 10 ohm-cm at 37° centigrade. The resistivity gradient at the electrolyte solution-mucosal layer interface is now 10/500, rather than 70/500 when, as previously described, bile carried the radiofrequency current. The steeper resistivity gradient enhances selective power deposition and heating in the mucosal layer.

Depicted in FIG. 2 is a cross-sectional view of the elongated member 103 of the catheter. The elongated member includes a plurality of lumens 201–204 that extend the entire longitudinal length of the member. Filling lumen 201 is for transporting the electrolyte solution from the proximal end 115 of the catheter to the distal end 105. As shown in FIG. 1, a plurality of side ports 108 about the distal end connected to filling lumen 201 facilitates the expansion of capacitive balloon electrode 106. The balloon electrode is attached in a well-known manner to the distal end of the catheter and expands with the electrolyte solution to make electrical and physical contact with mucosal layer 101 of the gallbladder. The balloon electrode also contains the electrolyte solution and prevents caustic solutions from causing possible undesired injury to surrounding tissue. The shape of the gallbladder conforms to the expanded electrode to provide a more even distribution of radiofrequency current to the mucosal layer. Positioning of the balloon electrode and contact with the mucosal layer is visualized and verified by any one of a number well-known techniques such as fluoroscopy. Such technique is enhanced with the radio-opaque electrolyte solution.

The balloon electrode comprises a thin wall or layer of material, such as well-known latex, having a thickness ranging from two to ten thousandths of an inch. Since the balloon wall is very thin, the capacitance thereof is thus quite large approximating, for example, 10,000 pF. The reactance of this capacitive electrode to, for example, a two megahertz radiofrequency current signal is thus relatively low such as 7 ohms. As a result, the radiofrequency signal is negligibly impeded by the balloon wall.

A second lumen 202 included in elongated member 103 transports gallbladder bile from distal end 105 of the catheter to proximal end 115 for drainage therefrom. Depicted in FIG. 4 is an enlarged view of the distal end of elongated member 103. This drainage occurs as a result of expanding the balloon electrode and consequently forcing the gallbladder bile into the drainage lumen.

Positioned about the distal end 105 of the catheter is sensor 109 such as a well-known thermistor for sensing the temperature of the surrounding environment. A volume of this environment includes the current-emitting electrode, the electrolyte solution and the mucosal layer of the gallbladder. Since a direct reading of the mucosal layer temperature is not practically feasible, the temperature of the electrolyte solution and current-emitting electrode are utilized to closely approximate the temperature of mucosal layer 101. This approximation is derived from a number of experimental measurements along with knowing the power deposition characteristics of the radiofrequency current from the current-emitting electrode as previously described with respect to the spherical model. A third lumen 203 in member 103 of the catheter provides a channel for extending a pair of electrical conductors 110 that are connected to temperature sensor 109.

The electrical conductors from the thermistor are connected to a well-known control circuit 113 included in radiofrequency generator 112 for controlling the amount of current supplied to current-emitting electrode 104 as a function of temperature. The sensed temperature is used to control the amount of current supplied to the current-emitting electrode so as to maintain the temperature of mucosal layer 101 at a temperature such as 50° centigrade to thermally coagulate and destroy the layer. Since the power deposition gradient is the steepest at the mucosal layer, the outer layer 115 of the gallbladder is not thermally destroyed since the temperature therein is less than the 42° centigrade temperature necessary to thermally destroy living tissue.

A fourth lumen 204 is also included in elongated member 103 for housing an electrical conductor 111 for interconnecting current-emitting electrode 104 and radiofrequency current generator 112. A large dispersive electrode 120 is placed on the skin 121 of the patient's body (not shown) to receive the radiofrequency current emitted from the balloon electrode and conducted through the body of the patient and to reduce trauma to the body. Another electrical conductor 116 interconnects the dispersive electrode and the radiofrequency current generator.

The method for thermally destroying, or more specifically, thermally coagulating the mucosal layer of the gallbladder includes inserting the distal end of the catheter into body 114 of gallbladder 102 endoscopically by a retrograde route through the duodenum, common bile duct and cystic duct. The capacitive balloon electrode is then expanded with the electrolyte solution for making electrical and physical contact with the gallbladder. The balloon catheter also conforms the gallbladder thereto to provide a more uniform distribution of the radiofrequency current from the current-emitting electrode. The use of the electrolyte solution with a resistivity lower than gallbladder bile and of the thin wall balloon electrode permits the concentrated deposition of power within the mucosal layer of the gallbladder. This concentrated deposition of power causes the selective heating of the mucosal layer to a thermally destructive temperature without destroying or killing outer layer 122 of the gallbladder. The mucosal layer of the cystic duct is also thermally destroyed to prevent the recurrence of gallstones therein. The temperature of the mucosal layer is maintained at a predetermined temperature such as 50° centigrade for a predetermined period of time to ensure the thermal coagulation and thermal destruction of the entire mucosal layer. Heating times for thermally coagulating and destroying the mucosal layer of the gallbladder in dogs has been derived from experiments in which heating times varied from 6-15 minutes at approximately 50° C. for dogs ranging in weight from 8-23 kg. The percentage of mucosal layer destroyed varied from 90-100%.

It is to be understood that the above-described method and apparatus for thermally destroying the layer of an organ is merely an illustrative embodiment of the principles of this invention and that other apparatus and methods may be devised by those skilled in the art without departing from the spirit and scope of this invention. In particular, different electrolyte solutions with varying resistivities may be employed along with different degrees of radio-opacity. In another embodiment, the capacitive balloon electrode may be eliminated and the distal end of the elongated member slit along the longitudinal axis thereof to form several strips therein. The current-emitting electrode is internally affixed to the distal tip of the member and operated to expand the strips radially and hold the electrode in the center of the gallbladder. The expanded strips engage and make contact with the inner mucosal layer of the gallbladder. Experiments with this conductive electrode catheter indicated that an electrode temperature of 72° was needed to maintain the mucosal layer at 50° C. while the outer wall temperature was approximately 41° C. The radiofrequency generator utilized in these experiments had a tentative frequency of two megahertz with signal amplitude ranging between 0-2 amps rms of radiofrequency current.

What is claimed is:

1. Apparatus for thermally destroying a layer of an organ comprising:
    an elongated member including a single fluid-transporting lumen opening interior to a capacitive balloon electrode;
    a current-emitting electrode positioned about a distal end of said member and connectable to a source of radiofrequency current for emitting radiofrequency current; and
    said capacitive balloon electrode surrounding said current-emitting electrode for distributing said current to said layer and having a shape expandable in response to an electrolyte solution for conforming said layer thereto, whereby said balloon electrode and said electrolyte solution in a non-flowing state cooperate in response to said radiofrequency current for selectively depositing power in said layer when said layer is in contact with said balloon electrode.

2. The apparatus of claim 1 wherein said lumen includes a plurality of ports about said distal end of said elongated member for expanding said balloon electrode.

3. The apparatus of claim 1 wherein said member comprises a lumen opening exterior to said balloon electrode for draining fluid from said organ displaced by said balloon electrode.

4. The apparatus of claim 1 further comprising sensor means for sensing a temperature of an environment about said distal end of said member.

5. The apparatus of claim 5 wherein said sensor means includes a thermistor.

6. The apparatus of claim 5 wherein said member includes a lumen in said elongated member reading to said sensor means.

7. The apparatus of claim 1 wherein said elongated member includes a lumen in said elongated member leading to said current-emitting electrode.

8. The apparatus of claim 1 wherein said capacitive balloon electrode comprises a flexible material having a predetermined capacitance.

9. The apparatus of claim 1 further comprising said source of radiofrequency current connected to said current-emitting electrode.

10. The apparatus of claim 9 further comprising means responsive to a temperature of an environment about said distal end of said member for controlling said source of radiofrequency current.

11. The apparatus of claim 1 further comprising said electrolyte solution including a radio-opaque compound.

12. A catheter for thermally coagulating the mucosal layer of a gallbladder, said mucosal layer having a first predetermined resistivity, comprising:
an elongated member having a distal end and a plurality of lumens therein;
a capacitive balloon electrode attached about said distal end of said elongated member and including a flexible material having a predetermined capacitance for making contact with said mucosal layer and for containing an electrolyte solution;
a first one of said lumens having a plurality of ports opening interior to said balloon electrode for expanding said balloon electrode with said electrolyte solution;
said solution having a second predetermined resistivity less than said first predetermined resistivity of said mucosal layer for selectively heating said mucosal layer;
a current-emitting electrode positioned about said distal end of said elongated member for emitting radiofrequency current to said balloon electrode and said mucosal layer when said balloon electrode is in contact with said mucosal layer, said current for heating said mucosal layer to a predetermined temperature, the heating of said mucosal layer at said predetermined temperature for a predetermined time period thermally coagulating said mucosal layer;
an electrical conductor connected to said current-emitting electrode and in a second one of said lumens for conducting said current from a source of said current to said current-emitting electrode;
a thermistor positioned about said distal end for sensing a temperature of an environment about said distal end;
a pair of electrical conductors in a third one of said lumens and connected to said thermistor for sending said sensed temperature to a current control circuit; and
a fourth one of said lumens opening exterior to said balloon electrode for draining fluid from said gallbladder when said balloon electrode is being expanded with said electrolyte solution.

13. Apparatus for thermally destroying a layer of an organ, comprising:
an elongated member including first and second lumens therein, said first lumen opening interior to a capacitive balloon electrode, said second lumen opening exterior to said balloon electrode;
a current-emitting electrode positioned about a distal end of said member and connectable to a source of radiofrequency current for emitting radiofrequency current; and
said capacitive balloon electrode positioned about said distal end and surrounding said current-emitting electrode for distributing said current to said layer and expandable in response to an electrolyte solution for making contact with said layer and for containing said electrolyte solution, whereby said balloon electrode and said electrolyte solution cooperate in response to said radiofrequency current for selectively heating said layer of said organ.

14. A catheter for thermally destroying the mucosal layer of a gallbladder, comprising:
an elongated member including a single fluid-transporting lumen opening interior to a capacitive balloon electrode;
a current-emitting electrode positioned about a distal end of said member and connectable to a source of radiofrequency current for emitting radiofrequency current; and
said capacitive balloon electrode surrounding said current-emitting electrode and having a predetermined ellipsoidal shape expandable in response to an electrolyte solution for conforming said mucosal layer thereto, whereby said balloon electrode and said electrolyte solution in a non-flowing state cooperate in response to said radiofrequency current for selectively heating said mucosal layer.

15. A method for thermally destroying a layer of an organ comprising the steps of:
inserting into said organ next to said layer of expandable, capacitive balloon electrode positioned about a distal end of a catheter;
expanding said capacitive balloon electrode with an electrolyte solution for making contact with said layer;
maintaining said electrolyte solution in a nonflowing state;
distributing a radiofrequency current from said capacitive balloon electrode to said layer; and
responsive to said radiofrequency current, heating said layer to a predetermined temperature for a predetermined period of time for thermally destroying said layer.

16. The method of claim 15 wherein said heating includes selectively depositing power in said layer in response to said radiofrequency current.

17. The method of claim 16 wherein said depositing includes expanding said capacitive balloon electrode with an electrolyte solution having a predetermined resistivity less than the resistivity of said layer.

18. The method of claim 15 further comprising monitoring a temperature of an environment about said distal end and maintaining a temperature of said layer at said predetermined temperature for said predetermined period of time in response to said temperature of said environment.

19. The method of claim 15 wherein said expanding includes expanding said capacitive balloon electrode with an electrolyte solution having a second predetermined resistivity less than a first resistivity of said layer.

20. The method of claim 15 further comprising draining fluid from said organ displaced by said capacitive balloon electrode.

21. The method of claim 15 wherein said distributing includes emitting said radiofrequency current from a current-emitting electrode positioned within said capacitive balloon electrode.

22. The method of claim 15 further comprising verifying the position of said capacitive balloon electrode next to said layer.

* * * * *